(12) United States Patent
Chesney et al.

(10) Patent No.: US 6,331,161 B1
(45) Date of Patent: Dec. 18, 2001

(54) METHOD AND APPARATUS FOR FABRICATING A PRESSURE-WAVE SENSOR WITH A LEVELING SUPPORT ELEMENT

(75) Inventors: Charles F. Chesney, Sunfish Lake, MN (US); Michael Terry Riggs, Batavia, NY (US); Charles A. Lemaire, Apple Valley, MN (US)

(73) Assignee: Hypertension Diagnostics, Inc, Eagan, MN (US)

( * ) Notice: Subject to any disclaimer, the term of this patent is extended or adjusted under 35 U.S.C. 154(b) by 0 days.

(21) Appl. No.: 09/394,301

(22) Filed: Sep. 10, 1999

(51) Int. Cl.⁷ ........................................................ A61B 5/00
(52) U.S. Cl. .......................................... 600/485; 600/500
(58) Field of Search ..................................... 600/485, 486, 600/488, 500, 561

(56) References Cited

U.S. PATENT DOCUMENTS

| 3,651,353 |   | 3/1972 | Hugli et al. ............................ 310/8.4 |
| 3,724,274 | * | 4/1973 | Milalr ..................................... 600/488 |
| 3,946,724 | * | 3/1976 | La Balme .............................. 600/488 |

(List continued on next page.)

FOREIGN PATENT DOCUMENTS

| 0357275A1 |   | 3/1990 | (EP) ................................. A61B/5/11 |
| 87/02233  |   | 4/1987 | (WO) ............................... A61B/7/04 |
| 92/09232  |   | 6/1992 | (WO) ........................... A61B/5/0255 |
| 94/05207  |   | 3/1994 | (WO) ............................... A61B/7/04 |
| 95/06525  |   | 3/1995 | (WO) ............................... B06B/1/06 |

OTHER PUBLICATIONS

"Acoustic Contact Sensor", *Apollo Research Corp.*, Model 701010, 1–5, (1997).
"Aging Arteries", *Harvard Heart Letter*, 8(2), 4 pgs., (Oct. 1997).
"Guide to Modern Piezoelectric Ceramics", Advertising Material from Morgan Matroc, Inc. (undated), 6 pages.
"Nellcor's N–CAT Continuous Noninvasive Blood Pressure Monitor, Model N–500", Product Publication by Nellcor, Inc., 9 pages, 1991.
"Harvard Heart Letter", *Harvard Medical School*, 7(7), 5 pages (Mar. 1997).
"Non–Invasive Arterial Waveform Analysis and Blood Pressure Measurement", Pulse Dynamic Oscillometrics Clinical Information, Pulse Metric, Inc., San Diego, CA, 4.
"Non–Invasive Blood Pressure/Pulse Rate Monitoring and Recording System", PortfolioTM Health Series, 6 pages.

(List continued on next page.)

*Primary Examiner*—Robert L. Nasser
(74) *Attorney, Agent, or Firm*—Schwegman, Lundberg, Woessner & Kluth, P.A.

(57) ABSTRACT

A method and an apparatus for fabricating a pressure-waveform sensor with a leveling support element. One embodiment provides a pressure-waveform sensor having a housing, a support element, and a piezoelectric element having a first end secured between the support element and the housing, and a second end in a cantilevered orientation. The support element and the piezoelectric element together form a plurality of support regions to level the piezoelectric element and relative to the housing. In some embodiments, the support element includes a ring having three slots spaced apart on one face of the ring, or one or more support regions formed with a shim having a thickness equal to a thickness of the piezoelectric device, or support regions that are integral to the support element. Another aspect provides a method for fabricating a pressure-waveform sensor. The method includes the steps of forming a housing structure with an inner lip, and supporting a cantilevered piezoelectric element with a support structure such that contact is made with the inner lip at a plurality of points in order to level the piezoelectric element relative to the inner lip.

22 Claims, 11 Drawing Sheets

U.S. PATENT DOCUMENTS

| | | | |
|---|---|---|---|
| 4,409,983 | 10/1983 | Albert | 128/690 |
| 4,431,873 | 2/1984 | Dunn et al. | 179/110 A |
| 4,548,205 * | 10/1985 | Armeniades et al. | 600/488 |
| 4,672,976 | 6/1987 | Kroll | 128/715 |
| 4,784,154 | 11/1988 | Shirley et al. | 128/715 |
| 4,889,133 | 12/1989 | Nelson et al. | 128/681 |
| 4,947,859 | 8/1990 | Brewer et al. | 128/715 |
| 4,949,710 | 8/1990 | Dorsett et al. | 128/680 |
| 4,974,596 * | 12/1990 | Frank | 600/488 |
| 4,993,422 | 2/1991 | Hon et al. | 128/672 |
| 5,035,247 | 7/1991 | Heimann | 128/715 |
| 5,211,177 | 5/1993 | Chesney et al. | 128/691 |
| 5,240,007 | 8/1993 | Pytel et al. | 128/672 |
| 5,241,964 | 9/1993 | McQuilkin | 128/672 |
| 5,269,312 | 12/1993 | Kawamura et al. | 128/690 |
| 5,316,004 | 5/1994 | Chesney et al. | 128/672 |
| 5,337,750 | 8/1994 | Walloch | 128/680 |
| 5,524,637 | 6/1996 | Erickson | 128/779 |
| 5,544,651 | 8/1996 | Wilk | 128/633 |
| 5,551,437 | 9/1996 | Lotscher | 128/672 |
| 5,551,438 | 9/1996 | Moses | 128/672 |
| 5,560,366 | 10/1996 | Harada et al. | 128/681 |
| 5,577,508 | 11/1996 | Medero | 128/681 |
| 5,584,298 | 12/1996 | Kabal | 128/672 |
| 5,590,661 | 1/1997 | Ohmori et al. | 128/672 |
| 5,592,401 | 1/1997 | Kramer | 364/550 |
| 5,617,868 | 4/1997 | Harada et al. | 128/672 |
| 5,623,933 | 4/1997 | Amano et al. | 128/687 |
| 5,638,823 | 6/1997 | Akay et al. | 128/691 |
| 5,640,964 | 6/1997 | Archibald et al. | 128/672 |
| 5,642,733 | 7/1997 | Archibald et al. | 128/672 |
| 5,647,369 | 7/1997 | Petrucelli et al. | 128/672 |
| 5,649,542 | 7/1997 | Archibald et al. | 128/681 |
| 5,671,750 | 9/1997 | Shinoda | 128/672 |
| 5,704,362 | 1/1998 | Hersh et al. | 128/280 |
| 5,752,919 | 5/1998 | Schrimpf | 600/493 |
| 6,019,729 * | 2/2000 | Itoigawa et al. | 600/488 |
| 6,132,382 * | 10/2000 | Archibald et al. | 600/500 |
| 6,159,166 * | 12/2000 | Chesney et al. | 600/502 |

OTHER PUBLICATIONS

Bing et al., Reversal of Acetylcholine Effect on Atherosclerotic Coronary arteries by Estrogen: Pharmacologic Phenomenon of Clinical Importance?, *Journal of the American college of Cardiology*, 3 pages, (Aug. 1992).

Brinton, et al., "Arterial Compliance by Cuff Sphygmomanometer", *Hypertension*, 28(4), Application to Hypertension and Early Changes in Subjects at Genetic Risk, 599–603, (Oct. 1996).

Brinton, et al., "The Development and Validation of a New Non–invasive Method to Evaluate Ventricle Function During Routine Blood Pressure Monitoring", *American Journal of Hypertension*, 10(4) Part2 (Abstract Issue), 2 pages, (1997).

Cohn, J.N., et al., "Noninvasive Pulse wave Analysis for the early detection of Vascular Disease", *Hypertension*, 26, 503–508, (Sep., 1995).

Glasser, et al., "Vascular Compliance and Cardiovascular Disease", *AJH, 10(10),Part* 175–1189, (Oct. 1997).

Kluger, J., "Beyond Cholesterol", *Time*, 48, (Aug. 4, 1997).

McVeigh, et al., "Vascular Abnormalities Associated with Long–term Cigarette Smoking Identified by Arterial Waveform Analysis", *The American Journal of Medicine*, 102, 227–231, (Mar. 1997).

Rajkumar, et al., "Hormonal Therapy Increases Arterial Compliance in Postmenopausal Women", *JACC*, 30(2), 350–356, (Aug. 1997).

Simon, et al., "Detection of Preclinical Atherosclerosis May Optimize the Management of Hypertension", *AJH*, 10(7) Part 1, 813–824, (Jul. 1997).

Yoshizawa, et al. "Classical but Effective Techniques for Estimating Cardiovascular Dynamics", *IEEE Engineering in Medicine & Biology Magazine*, 16(5), 106–112, (Sep.–Oct. 1997).

05491392

* cited by examiner

METHOD AND APPARATUS FOR FABRICATING A PRESSURE-WAVE SENSOR WITH A LEVELING SUPPORT ELEMENT

FIELD OF THE INVENTION

This invention relates to the field of medical sensors, and, more specifically, to a method and apparatus of sensing an arterial pulse pressure, and, in particular, the blood pressure waveform in the radial artery of the human body.

BACKGROUND OF THE INVENTION

Conventionally, blood pressure has been measured by one of four basic methods: invasive, oscillometric, auscultatory and tonometric. The invasive method, also known as an arterial-line method (or "A-line"), typically involves insertion of a needle or catheter into an artery. A transducer connected by a fluid column to the needle or catheter is used to determine exact arterial pressure. With proper instrumentation, systolic, diastolic, and mean arterial pressures may be determined, and a blood-pressure waveform may be recorded. This invasive method is difficult to set up, is expensive and time consuming, and involves a potential medical risk to the subject or patient (for example, formation of emboli or subsequent infection). Set up of the arterial-line method also poses technical problems. Resonance often occurs and causes significant errors. Also, if a blood clot forms on the end of the needle or catheter, or the end of the needle or catheter is located against an arterial wall, a large error may result. To eliminate or reduce these errors, the apparatus must be checked, flushed, and adjusted frequently. A skilled medical practitioner is required to insert a needle or catheter into the artery, which contributes to the expense of this method. Medical complications are also possible, such as infection, nerve and/or blood vessel damage.

The other three traditional methods of measuring blood pressure arc non-invasive. The oscillometric method measures the amplitude of blood pressure oscillations in an inflated cuff. Typically, the cuff is placed around the left upper arm of the patient and then pressurized to different levels. Mean pressure is determined by sweeping the cuff pressure and determining the cuff pressure at the instant the peak amplitude occurs. Systolic and diastolic pressure is determined by cuff pressure when the pressure oscillation is at some predetermined ratio of peak amplitude.

The auscultatory method also involves inflation of a cuff placed around the left upper arm of the patient. After inflation of the cuff to a point where circulation is stopped, the cuff is permitted to deflate. Systolic pressure is indicated when Korotkoff sounds begin to occur as the cuff is deflated. Diastolic pressure is indicated when the Korotkoff sounds become muffled or disappear.

The fourth method used to determine arterial blood pressure has been tonometry. The tonometric method typically involves a transducer positioned over a superficial artery. The transducer may include an array of pressure-sensitive elements. A hold-down force is applied to the transducer in order to partially flatten the wall of the underlying artery without occluding the artery. Each of the pressure-sensitive elements in the array typically has at least one dimension smaller than the lumen of the underlying artery in which blood pressure is measured. The transducer is positioned such that at least one of the individual pressure sensitive elements is over at least a portion of the underlying artery. The output from one or more of the pressure-sensitive elements is selected for monitoring blood pressure. These tonometric systems either use an upper-arm cuff to calibrate blood-pressure values, or they measure a reference pressure directly from the wrist and correlate this with arterial pressure. However, when a patient moves, recalibration of the tonometric system is often required because the system may experience a change in electrical gains. Because the accuracy of such tonometric systems depends upon the accurate positioning of the individual pressure sensitive element over the underlying artery, placement of the transducer is critical. Consequently, placement of the transducer with these tonometric systems is time-consuming and prone to error. Also, expensive electro-mechanical systems guided by software/hardware computer approaches are often used to assist in maintaining transducer placement.

The oscillometric, auscultatory and tonometric methods measure and detect blood pressure by sensing force or displacement caused by blood pressure pulses within the underlying artery that is compressed or flattened. The blood pressure is sensed by measuring forces exerted by blood pressure pulses in a direction perpendicular to the underlying artery. However, with these methods, the blood pressure pulse also exerts forces parallel to the underlying artery as the blood pressure pulses cross the edges of the sensor which is pressed against the skin overlying the underlying artery of the patient. In particular, with the oscillometric and the auscultatory methods, parallel forces are exerted on the edges or sides of the cuff. With the tonometric method, parallel forces are exerted on the edges of the transducer. These parallel forces exerted upon the sensor by the blood pressure pulses create a pressure gradient across the pressure-sensitive elements. This uneven pressure gradient creates at least two different pressures, one pressure at the edge of the pressure-sensitive element and a second pressure directly beneath the pressure sensitive element. As a result, the oscillometric, auscultatory and tonometric methods can produce inaccurate and inconsistent blood pressure measurements.

Further, the oscillometric and auscultatory methods are directed at determining the systolic, diastolic, and/or mean blood pressure values, but are not suited to providing a calibrated waveform of the arterial pulse pressure.

The traditional systolic-diastolic method for measuring blood pressure provides the physician with very limited clinical information about the patient's vascular health. In contrast, the HDI/PulseWave™ DO-2020 system made by Hypertension Diagnostics, Inc., the assignee of the present invention, measures a blood pressure waveform produced by the beating heart that, it is believed, can be analyzed to provide an assessment of arterial elasticity. When the aortic valve closes after the heart has ejected its stroke volume of blood (the blood ejected during each heart beat), the decay or decrease of blood pressure within the arteries prior to the next heart beat forms a pressure curve or waveform which is indicative of arterial elasticity. Subtle changes in arterial elasticity introduce changes in the arterial system that are reflected in the arterial blood pressure waveform and research suggests that these changes in the function and structure of the arterial wall precede the development of coronary artery disease, or the premature stiffening of the small arteries which appears to be an early marker for cardiovascular disease.

Incorporating the physiological phenomena associated with blood pressure waveforms, Drs. Jay N. Cohn and Stanley M. Finkelstein, Professors at the University of Minnesota in Minneapolis, developed in the early 1980's a method for determining a measure of elasticity in both large and small arteries. That technique involved an invasive procedure that placed a catheter connected to a pressure transducer into the patient's artery in order to obtain a blood pressure waveform that could be analyzed using a modified Windkessel model, a well-established electrical analog model which describes the pressure changes during the diastolic phase of the cardiac cycle in the circulatory system.

This "blood pressure waveform" or "pulse contour" analysis method provided an independent assessment of the elasticity or flexibility of the large arteries which expand to briefly store blood ejected by the heart, and of the small arteries (arterioles) which produce oscillations or reflections in response to the blood pressure waveform generated during each heart beat.

By assessing the elasticity of the arterial system, clinical investigators have been able to identify a reduction in arterial elasticity in patients without evidence of traditional risk factors, suggesting the early presence of vascular disease. Furthermore, clinical research data has demonstrated that individuals with heart failure, coronary artery disease, hypertension and diabetes typically exhibit a loss of arterial elasticity. These abnormal blood vessel changes often appear to precede overt signs of cardiovascular disease and the occurrence of a heart attack or stroke by many years. Clinical investigators have also demonstrated an age-related loss of elasticity of both the large and small arteries suggesting that premature stiffening of an individual's arteries is an apparent marker for the early onset of cardiovascular disease.

There is a need to obtain, non-invasively, an accurate, repeatable blood-pressure waveform from the radial artery, in order to avoid the problems associated with invasive procedures such as those described above.

In particular, a sensor approximately ½" in diameter and approximately ½" in height has been found to provide good results. However, the construction of such a sensor is difficult due to its small size and need to be rigged, sealed, and accurate. Thus there is a need for an improved sensor structure and method.

SUMMARY OF THE INVENTION

The invention includes a method and an apparatus for fabricating a pressure-wave (also called pressure-waveform) sensor with an improved support element. The support element precisely levels a piezoelectric element relative to the sensor housing. In one embodiment, the sensor is used for sensing an arterial-pulse-pressure waveform.

One embodiment provides a pressure-waveform sensor having a housing, a support element, and a piezoelectric element having a first end secured between the support element and the housing, and a second end in a cantilevered orientation. The support element and the piezoelectric element together form a plurality of support regions to level the piezoelectric element relative to the housing.

In some embodiments of the pressure-waveform sensor, the support element includes a ring having three slots spaced apart on one face of the ring, and having the piezoelectric element mounted to a first one of the slots. In one such embodiment, the ring further includes leveler elements mounted in a second and a third of the three slots to provide two of the support regions.

In one embodiment, one or more of the plurality of support regions are formed with a shim having a thickness equal to a thickness of the piezoelectric device. In some embodiments of the pressure-waveform sensor, the support element has a first face region for attaching to the first end of the piezoelectric element, and a second face region elevated and relative to the first face region to provide one or more of the plurality of support regions. In one such embodiment, the support regions of the second face region are integral to the support element.

Another aspect of the present invention provides a method for fabricating a pressure-waveform sensor. The method includes the steps of forming a housing structure with an inner lip, and supporting a cantilevered piezoelectric element with a support structure such that contact is made with the inner lip at a plurality of regions in order to level the piezoelectric element relative to the inner lip.

DESCRIPTION OF THE PREFERRED EMBODIMENT

In the following detailed description of the preferred embodiments, reference is made to the accompanying drawings which form a part hereof, and in which is shown by way of illustration, specific embodiments in which the invention may be practiced. It is to be understood that other embodiments may be utilized and structural changes may be made without departing from the scope of the present invention.

When measuring the pressure waveform from the radial artery in the human arm, a sensor approximately ½" in diameter and approximately ½" in height has been found to provide good results. One such sensor is described in patent application Ser. No. 09/045,018 entitled "SENSOR AND METHOD FOR SENSING ARTERIAL PULSE PRESSURE" and is assigned to the assignee of the present invention, and is incorporated herein by reference. Moreover, co-pending application Ser. No. 09/045,449 entitled "APPARATUS AND METHOD FOR HOLDING AND POSITIONING AN ARTERIAL PULSE PRESSURE SENSOR" and 09/045,420 entitled "APPARATUS AND METHOD FOR BLOOD PRESSURE PULSE WAVEFORM CONTOUR ANALYSIS" show ways of using the present invention, and are also incorporated herein by reference.

The invention described in this application is useful for many types of arterial-pulse-pressure sensing devices, including those having a piezoelectric element contained in a housing. The invention is useful with many mechanical configurations of leveling support elements.

Figure 1:
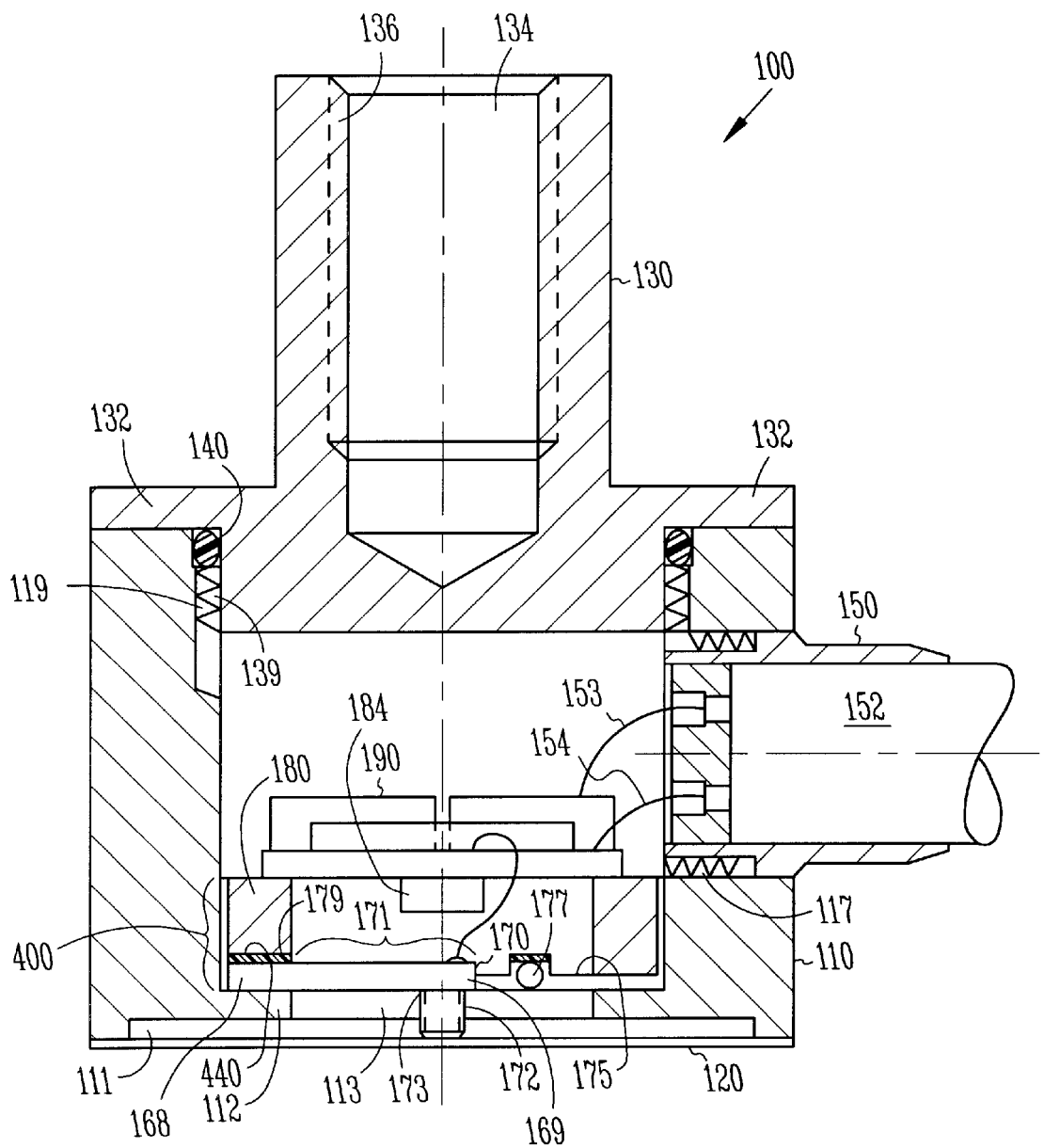
FIG. 1 shows a cross-section view of one embodiment of arterial pulse pressure sensor 100 with leveler element 177.

FIG. 1 shows a cross-section view of one embodiment of assembled arterial pulse pressure sensor 100. In the embodiment shown, arterial pulse pressure sensor 100 includes housing 110, diaphragm 120 which is welded to housing 110 (in one embodiment, laser welded), cover 130 which is screwed onto housing 110 and sealed using O-ring 140, cable adaptor 150 which is screwed to housing 110 and glued and sealed to signal/power cable 152 with epoxy, piezoelectric double-plate ceramic element (DPCE) 170 which is attached using epoxy between piezoelectric-element-holder ring 180 and shelf 112 of housing 110, and amplifier 190 which is mounted to piezoelectric-element-holder ring 180 (also generically called holder element 180, since other embodiments use a triangle, or a square, or a disc, or other suitable shape in place of the ring shown in this embodiment). Since one embodiment uses piezoelectric element 170, this embodiment is described as having first end 168 secured between piezoelectric element holder ring 180 and housing 110, and second end 169 in a cantilevered orientation 171, and piezoelectric-element post 172 attached to second end 169 of piezoelectric element 170. Contact point(s) 177 is the area or areas wherein support element 400 (or alternative 500, 600, 700, or 800) make mechanical (and optionally electrical) contact with inner lip 112 of housing 110. It is to be understood that other embodiments include single-plate ceramic piezoelectric elements or other types of pressure-sensing elements in place of DPCE 170, and will have a corresponding piezoelectric element holder ring 180 and post in some of those embodiments. The adjective term "DPCE" applies to those embodiments having a DPCE 170 sensing element, but not to other embodiments having other types of sensing elements.

In one embodiment, a piezoelectric double-plate ceramic element (DPCE) that is 0.021 inches thick is cut to 0.180 inches long and 0.050 inches wide. The top surface forms one electrical contact (to which a wire is soldered, and the wire is then attached to amplifier 190), and the bottom surface forms the other electrical contact (which is made by contact to housing shoulder 112) once DPCE-holder ring 180 is secured using epoxy. In one embodiment, piezoelectric DPCE 170 is a ceramic piezoelectric block cut from a bulk plate or sheet of Bimorph® material (e.g., from a sheet of PZT-5A originally measuring 1.5 inches long by 0.75 inches wide by 0.021 inches thick) available from Morgan Matroc, Inc., Electro Ceramics Division, Bedford, Ohio. Bimorph® is a registered tradename of Morgan Matroc, Inc., Electro Ceramics Division, for a double-plate ceramic element. The two thin plates are bonded together so they amplify their piezoelectric actions. A DPCE generates greater voltage when bent, deformed or displaced than does a single-plate ceramic element.

In various embodiments, support element 400 (or alternative support elements 500, 600, 700, or 800) is formed as a ring 180 or triangle or a square or disc or other shape not shown, that is used to support piezoelectric element 170, and optionally, to support amplifier 190. Support element 400 provides a two-pronged purpose. First, support element 400 provides reliable acoustic and mechanical contact for piezoelectric element 170 and post 172 with diaphragm 120. Therefore, the displacement coupling of piezoelectric element 170 with diaphragm 120 via post 172 is more reliable with one or more support regions (alternatively embodied as feet, shims, raised bumps, balls, or other leveling elements located either on support element 400 or housing 110 such that piezoelectric element 170 is provided level support). Second, support element 400 provides good electrical contact by leveling piezoelectric element 170 relative to housing 110, that is, the lower face of the first end 168 of piezoelectric element 170 is reliably in level contact with shelf 112 of housing 110, thus resulting in a good electrical connection. In one embodiment, a conductive adhesive such as epoxy is used between first end 168 of piezoelectric element 170 and shelf 112 of housing 110 to give better electrical contact. In other embodiments, no epoxy is used, such that the electrical contact is a mechanical butt joint.

In one embodiment, housing 110, diaphragm 120, cover 130, cable adaptor 150, and piezoelectric element holder ring 180 are medical-grade stainless steel (type 316L), in order to be durable and relatively inert for the intended use of skin-contact arterial pulse-pressure sensing. The piezoelectric element holder ring 180, in various embodiments, is made of stainless steel, plastic, ceramic or other suitable material and combinations thereof Deflection of diaphragm 120 causes piezoelectric element 170 to flex and thereby generate an electrical signal, which in turn is amplified and conditioned by amplifier 190 and coupled to signal/power cable 152 (also called input/output cable 152). Cable 152 provides both delivery of input electrical power to amplifier 190, as well as receiving the output signal from amplifier 190, all using only two signal conductors (e.g., input/output wire 153, and ground 154). In one embodiment, diaphragm 120 is displacementally coupled to second end 169 of the piezoelectric element 170. In one such embodiment, this displacement coupling is achieved by epoxying post 172 to second end 169, and locating the other end against diaphragm 120. Diaphragm 120 forms an insulating connection and an electrical connection. Moreover, diaphragm 120 provides structural support and proper alignment of piezoelectric element 170 as piezoelectric element 170 is inserted into housing 110. In one embodiment, cable 152 is connected to a constant-current source by connector 159 (e.g., a two-milliamp constant-current source), and amplifier 190 then provides a varying voltage (on the same signal wire that provides the constant current) linearly proportional to the pressure on diaphragm 120. An external circuit then receives and processes the arterial pulse-pressure waveform from the varying voltage. In some embodiments, the sensor 100 has amplifier 190 secured to a face of support element 400 opposite to the piezoelectric element 170.

Female threads 119 that are machined into the upper bore of housing 110 mate with male threads 139 of cover 130. O-ring gasket 140 forms a seal between housing 110 and cover 130. (In another embodiment, an O-ring gasket is also provided to seal between housing 110 and cable adaptor 150. In one preferred embodiment though, a potting epoxy is used instead of an O-ring to seal between housing 110 and cable adaptor 150.) Female threads 117 in the sidewall bore of housing 110 mate with male threads 157 of cable adaptor 150. In one embodiment, signal/power cable 152 is secured into the opening in cable adaptor 150 using epoxy, and cured in an oven at 150° F. for a minimum of 30 minutes. In one embodiment, holder ring 180 has slot 184 through one wall of the top face, and slot 440 through two walls of the bottom face. One end of piezoelectric element 170 is located mostly within slot 440 (i.e., the bottom surface of piezoelectric element 170 extends slightly below the bottom surface of holder ring 180 in order to make electrical and mechanical contact with shelf 112 of housing 110), but piezoelectric element 170 is electrically insulated from holder ring 180 by a layer of epoxy 179.

Figure 2:
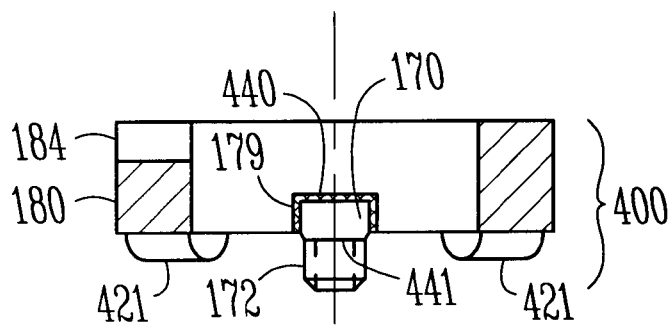
FIG. 2 shows a side view of the leveling support element 400 for a piezoelectric element 170.

FIG. 2 shows a side view of the leveling support element 400 for a piezoelectric element 170. The support element 400 and the piezoelectric element 170 together form a plurality of support regions 421, 441. As in FIG. 1, piezoelectric element holder ring 180 has a slot 184 through one wall on the top face of ring 180, and a slot 440 through one wall on the bottom face of ring 180. One end of piezoelectric element 170 is located mostly within slot 440 (i.e., the bottom surface of piezoelectric element 170 as shown in FIG. 1 extends slightly below the bottom surface of piezoelectric element holder ring 180 in order to make electrical and mechanical contact with shelf 112 of housing 110), but piezoelectric element 170 is electrically insulated from piezoelectric element holder ring 180 by a layer of epoxy 179. Ring 180, in various embodiments, is made of stainless steel, plastic, ceramic or other suitable material and/or combinations thereof. In various embodiments post 172 is made of stainless steel, plastic, ceramic or other suitable material and/or combinations thereof.

Figure 3:
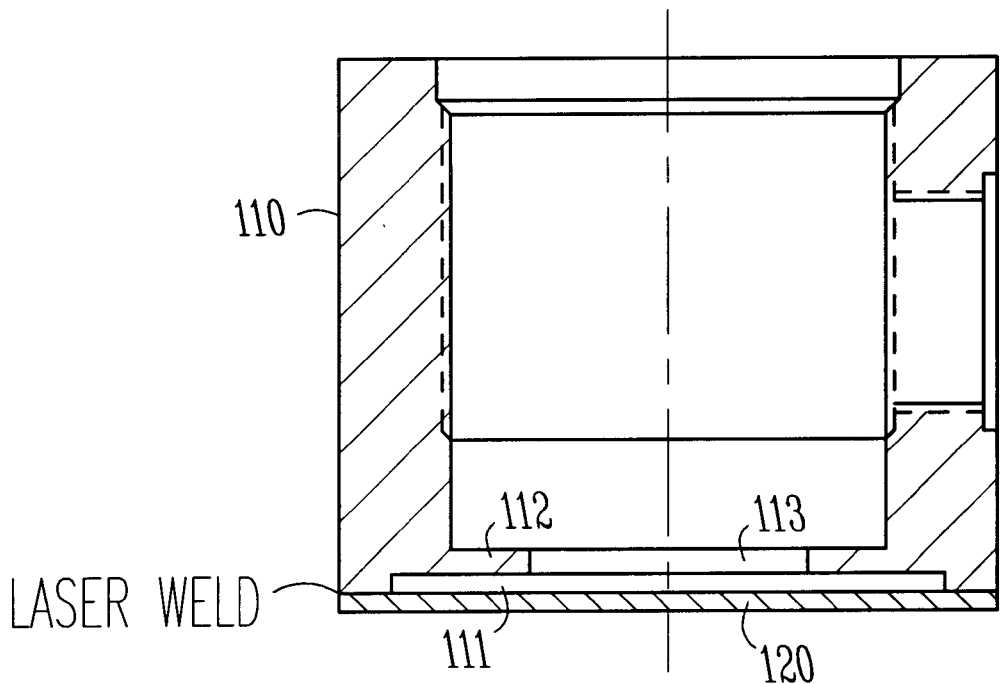
FIG. 3 shows a cross-section view of one embodiment of the housing 110.

FIG. 3 is a cross-section view of one embodiment of prior art housing 110 having diaphragm 120. In this embodiment, diaphragm 120 is a disc of medical-grade stainless steel (type 316L) having a diameter of 0.5 inches and a thickness of 0.006 inches. The thickness of diaphragm 120 is chosen to be thick enough to impart ruggedness and durability to arterial pulse pressure sensor 100, yet thin enough to provide the sensitivity and frequency response desired. In one embodiment, diaphragm 120 is laser-welded to the bottom surface of housing 110 across opening 111, using a pulsed NdYAG laser welder, with weld settings of: pulse rate—40/sec; pulse width—1; joules/pulse—0.3; and seconds/rev—5.5. Other types of welding such as Tungsten Inert Gas (TIG), may be used. A diaphragm welding pilot is used to hold the housing and a diaphragm welding heat sink is also used.

Figure 4A:
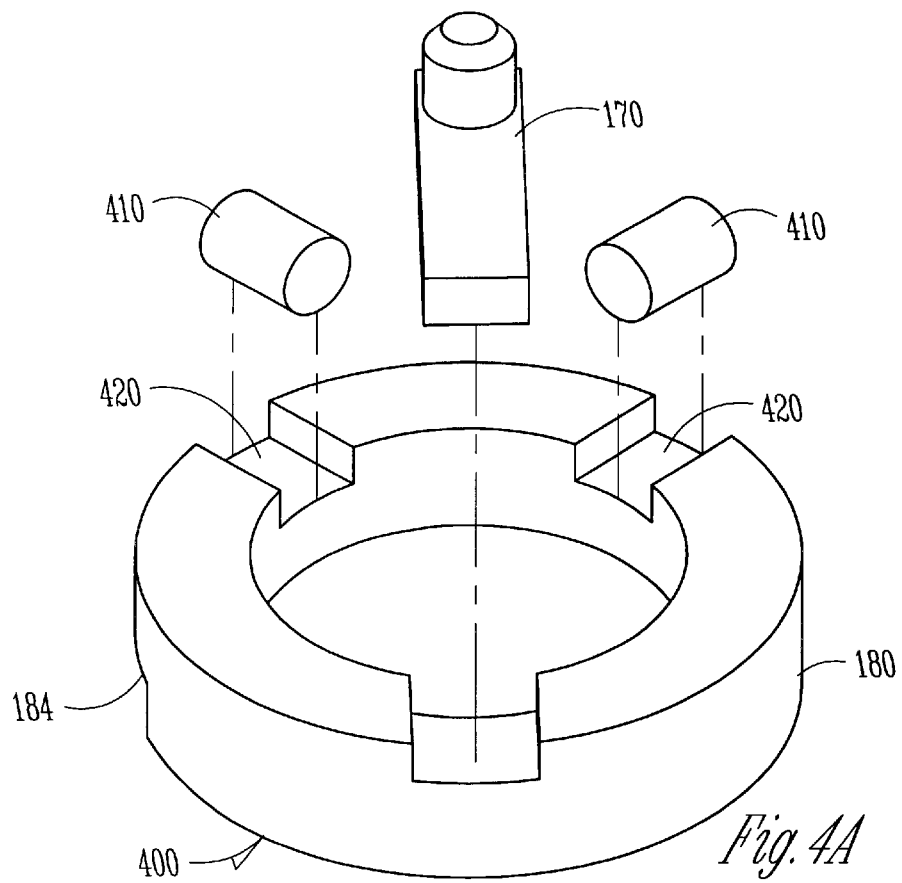
FIG. 4A shows an exploded isometric view of the unassembled leveling support element 400 for a piezoelectric element 170.

FIG. 4A is an exploded isometric view of one embodiment of support element 400 as a ring having two slots 420 and one slot 440 spaced apart on one face of ring 180, and having the piezoelectric element 170 with a post 172 mounted to a first one of the slots 440. In one embodiment, the three slots (two slots 420 and slot 440) are spaced about 120 degrees from one another on the ring. In one such embodiment, the support element 400 further includes wire leveler elements 410 mounted in a second slot 420 and a third slot 420 of the three slots in order to provide support regions.

Figure 4B:
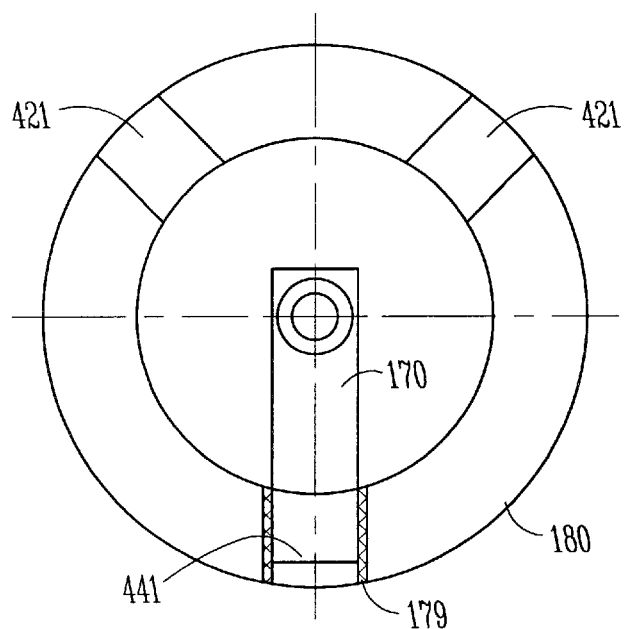
FIG. 4B shows a bottom view of the holder ring 180 with slots 421 and 441.

FIG. 4B is a bottom view of leveling support element 400 for piezoelectric element 170. In the embodiment shown, support element 400 and piezoelectric element 170 together form a plurality of support regions 421.

Figure 4C:
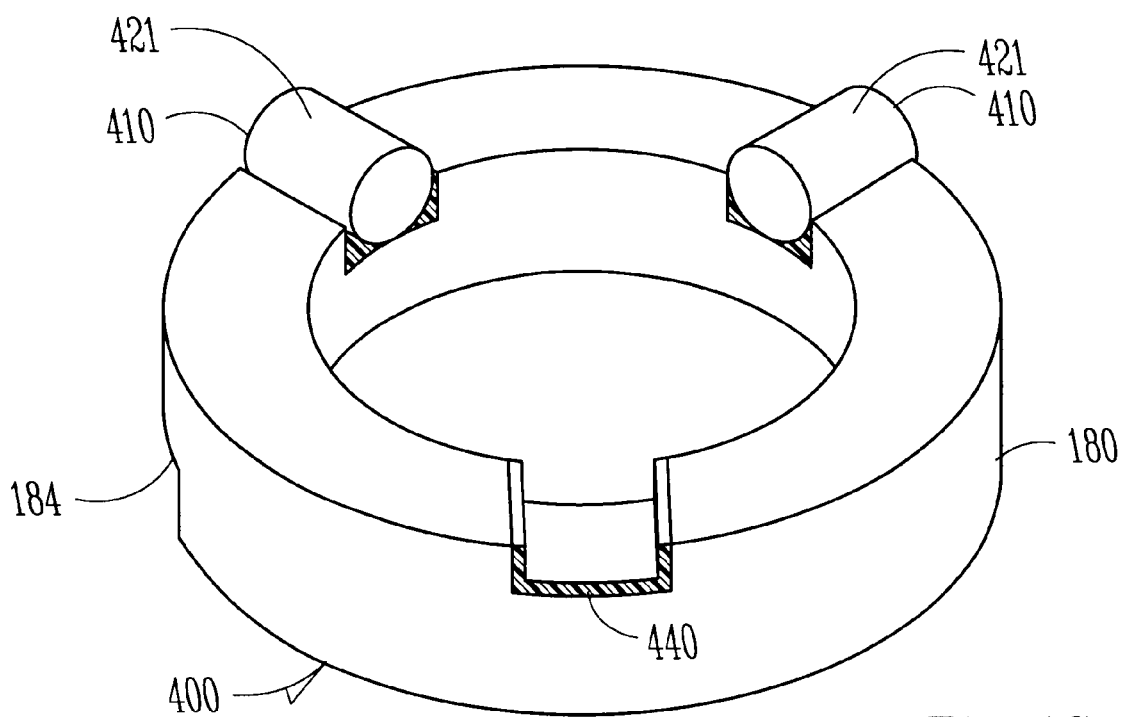
FIG. 4C shows an isometric view of an assembled leveling support element 400.

FIG. 4C is an isometric view of assembled support element 400 as a ring having support regions 421. The wire leveler elements are embedded within epoxy in slots 420. The support element 400 has slot 184 through one of its walls. Slot 440 for the piezoelectric element 170 is opposite of support regions 421. Epoxy is inserted in slot 440 prior to machining a small slot within the epoxy for piezoelectric element 170, in order that an insulating layer 179 of epoxy electrically insulates piezoelectric element 170 from holder element 180.

Figure 4D:
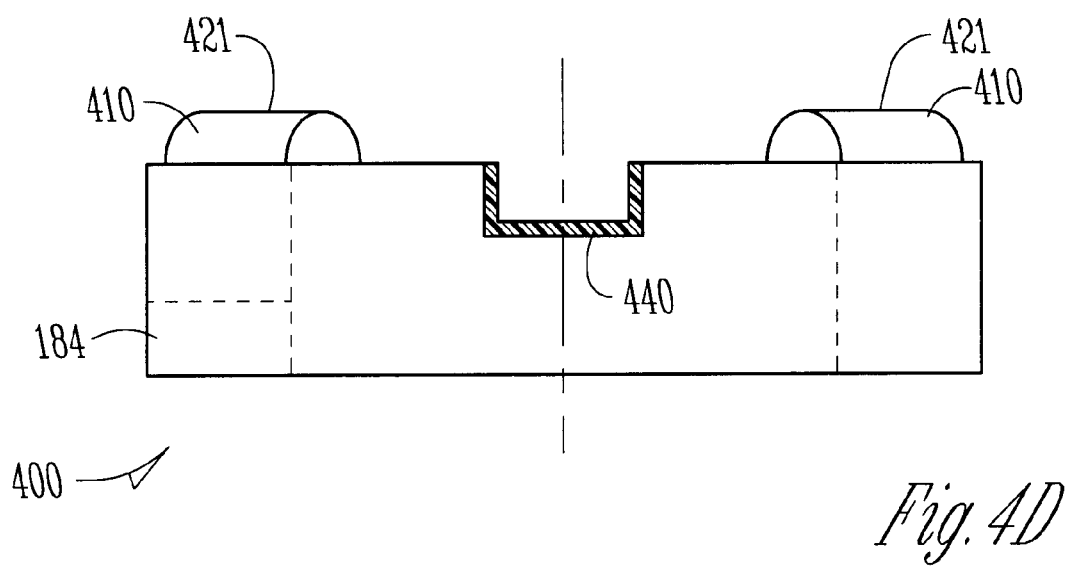
FIG. 4D shows a side view of the assembled leveling support element shown in FIG. 4D.

FIG. 4D is a side view of, support element 400 shown in FIG. 4C showing support regions 421 of support element 400.

Figure 5A:
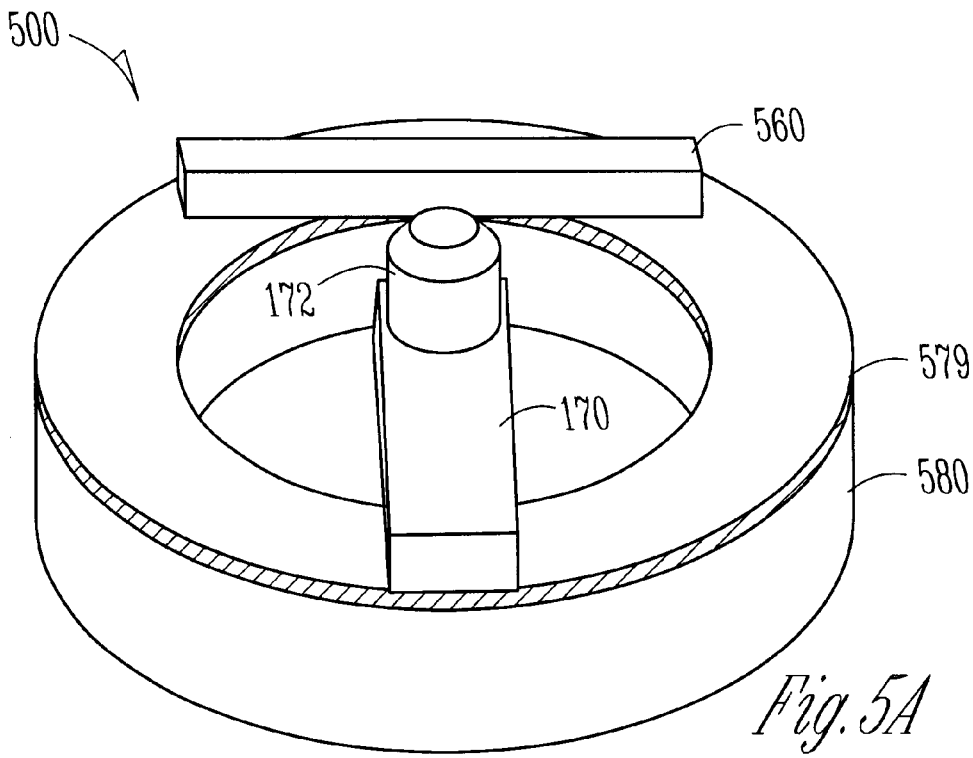
FIG. 5A shows an isometric view of the support element 500 and thin shim 560.

FIG. 5A is an isometric view of support element 500 and shim 560 atop its face. Shim 560 is thinner relative to piezoelectric element 170 because piezoelectric element sits atop ring 580. As used herein, the term shim can be flat, spherical, cylindrical or any other shape spacing element used to provide a leveling function. Also the present invention includes a raised feature integrally formed on another part such as feet in FIG. 6 and a raised or elevated lip in FIG. 8. Ring 580 has epoxy 579 providing insulating and electrical contact. In some embodiments, support element 500 is an alternative embodiment that can be substituted for support element 400 in the device shown in FIG. 1.

Figure 5B:
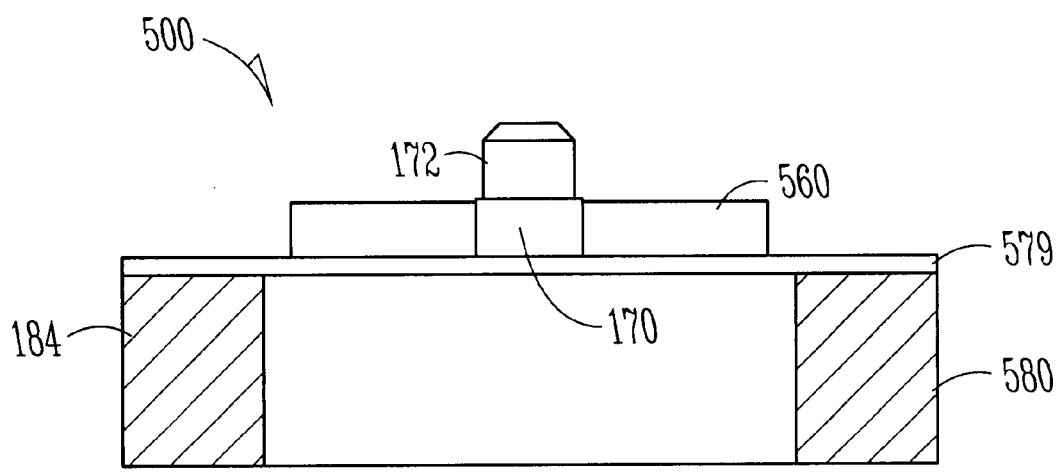
FIG. 5B shows a side view of the support element 500 and thin shim 560 shown in FIG. 5A.

FIG. 5B is a side view of support element 500 as shown in FIG. 5A. Each of the components are still visible from this view.

Figure 6:
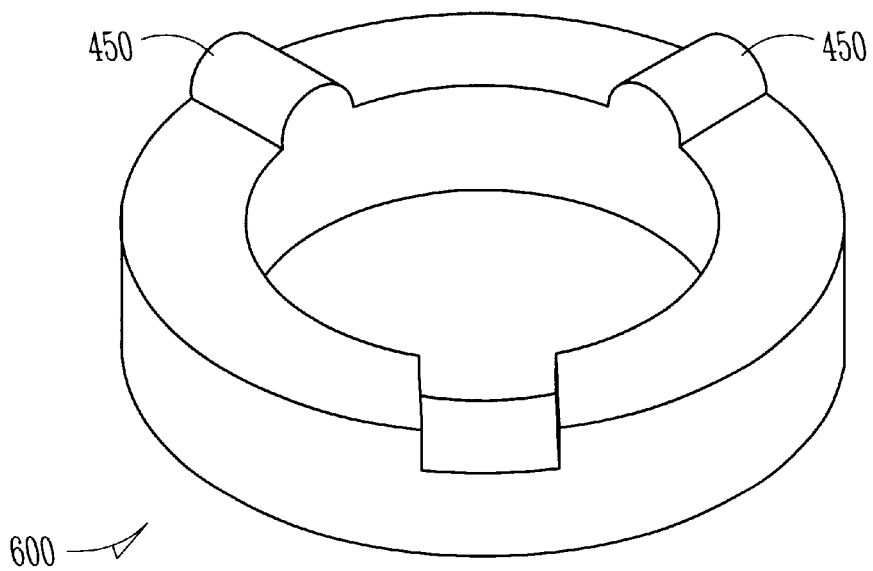
FIG. 6 shows an isometric view of a support element 600 with support regions 450.

FIG. 6 is an isometric view of support element 600 with integral support regions 450. In some embodiments, support element 600 is an alternative embodiment that can be substituted for support element 400 in the device shown in FIG. 1.

Figure 7A:
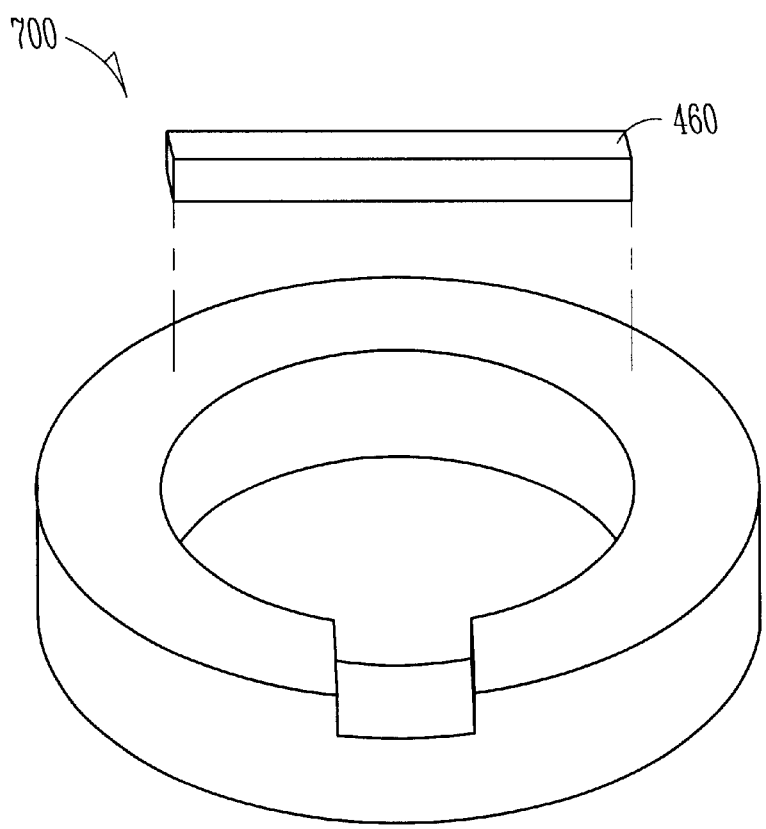
FIG. 7A shows an exploded isometric view of support element 700 including a shim 460.

FIG. 7A is an exploded isometric view of support element 700 includes a shim 460 having a thickness equal to a thickness of piezoelectric element 170, atop its face. In some such embodiments, shim 460 is thinner than the thickness of piezoelectric element 170, wherein piezoelectric element is recessed within slot 440. In some embodiments, shim 460 is equal in thickness to piezoelectric element 170, wherein both are mounted in relatively the same height on ring 180 and slot 440 has been eliminated. In some embodiments, shim 460 is thicker than piezoeletic element 170, wherein piezoelectric element 170 is seated in epoxy (thus providing an insulating spacer) on top of ring 180. In some embodiments, support element 700 is an alternative embodiment that can be substituted for support element 400 in the device shown in FIG. 1.

Figure 7B:
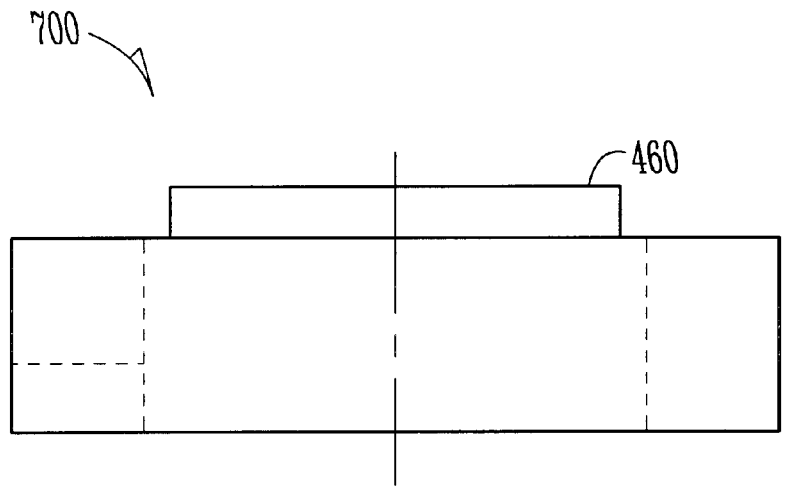
FIG. 7B shows a side view of the support element 700 having a shim 460 atop its face shown in FIG. 7A.

FIG. 7B is a side view of support element 700 shown in FIG. 7A showing the support element 700 having a shim 460 atop its face.

Figure 7C:
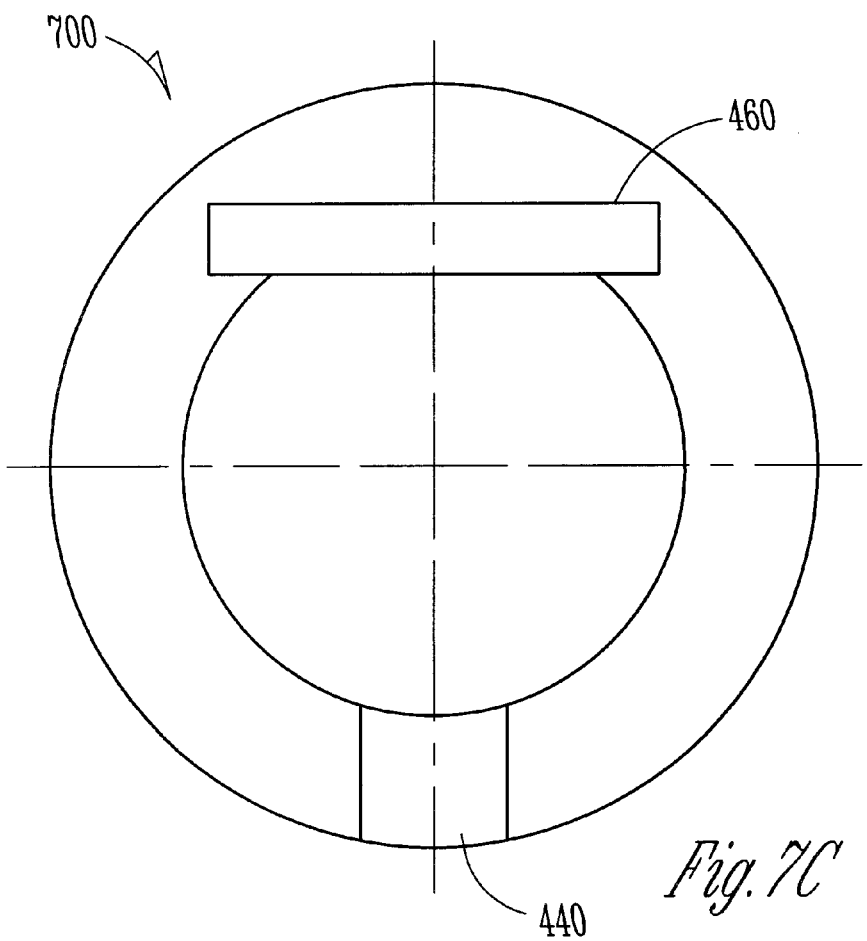
FIG. 7C shows a top view of the support element 700 having a shim 460 atop its face shown in FIG. 7A.

FIG. 7C is a top view of FIG. 7A showing support element 700 having a shim 460 atop its face.

Figure 8A:
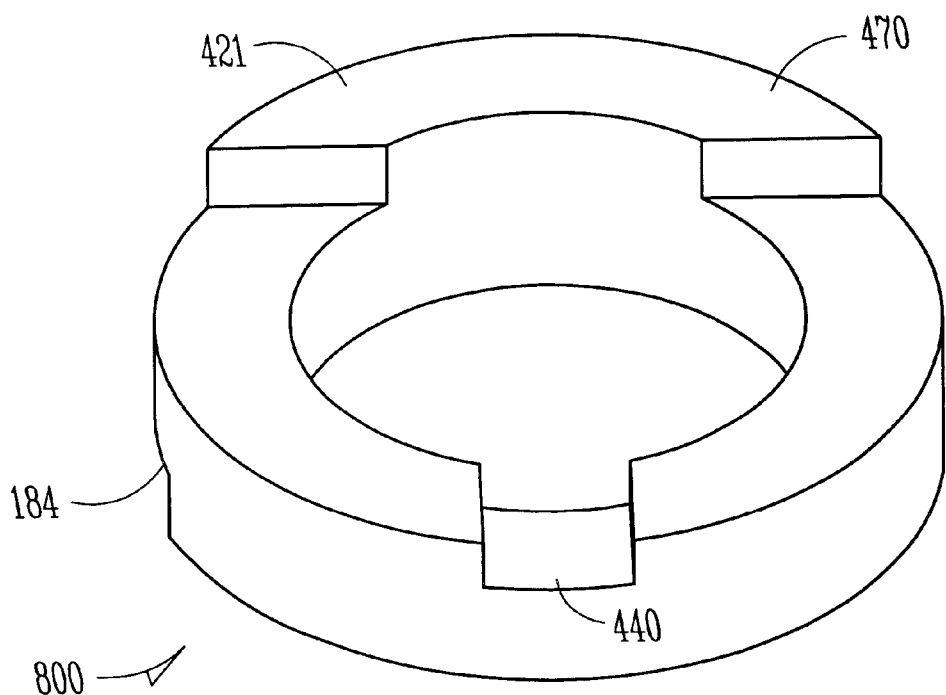
FIG. 8A shows an isometric view of support element 800 integrally formed with a shim 470.

FIG. 8A is an isometric view of support element 800 integrally formed with a raised region 470 having a thickness sufficient to level piezoelectric element 170. The support element 800 has slot 184 through one of its walls on the amplifier face and another slot 440 atop its face for the piezoelectric element. Slot 184 is 0.051 inches wide and 0.030 inches deep is machined in the upper surface, but only through one wall, as shown. Slot 184 is used as a reference during machining and assembly operations. In some embodiments of the pressure-waveform sensor 100, the support element 800 has a first face region (i.e., within slot 440) for attaching to the first end 168 of the piezoelectric element 170, and a second face region 470 elevated relative to the first face region 440 to provide one or more of the plurality of support regions 421. In one such embodiment, the support region or regions 421 of the second face region 470 are integral to the support element 800. In some embodiments, support element 800 is an alternative embodiment that can be substituted for support element 400 in the device shown in FIG. 1.

Figure 8B:
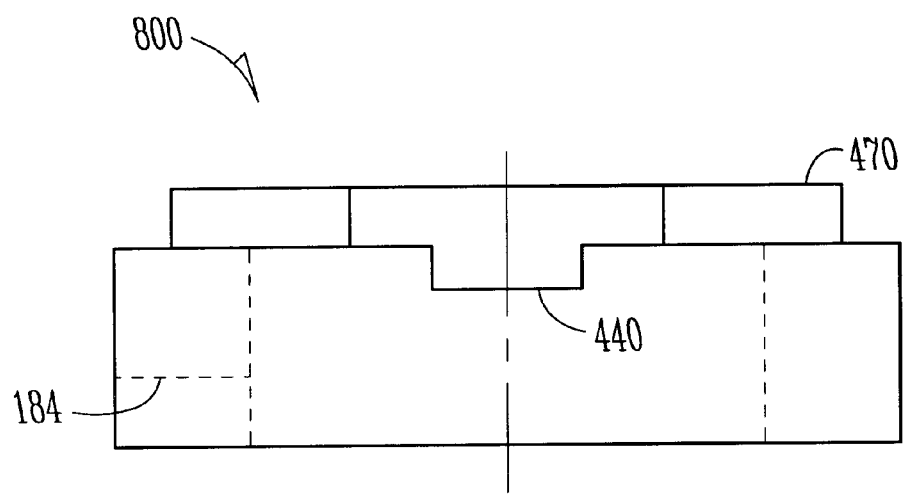
FIG. 8B shows a side view of support element 800 integrally formed with a shim 470 as shown in FIG. 8A.

FIG. 8B is a side view of support element 800 shown in FIG. 8A.

Figure 8C:
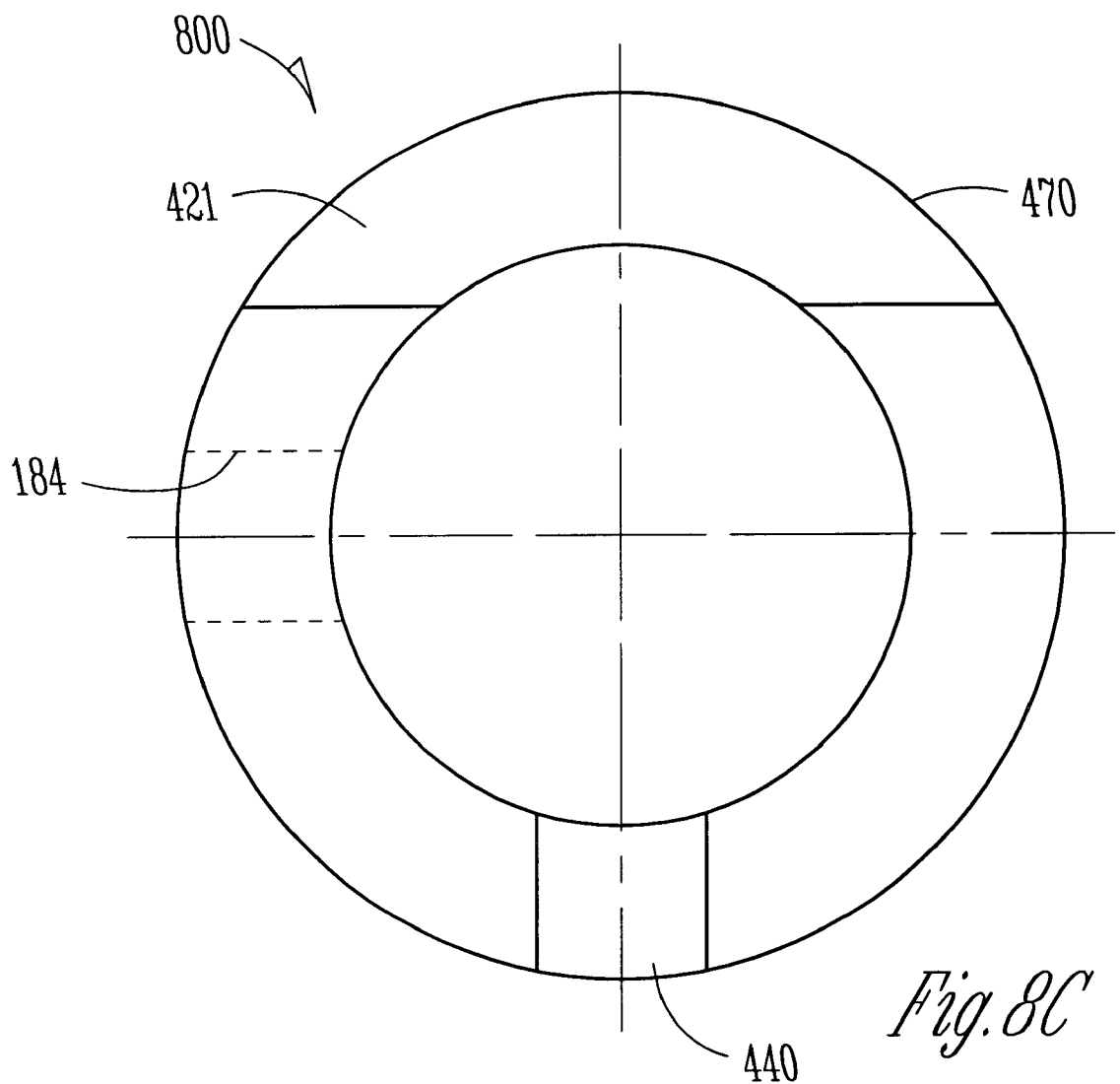
FIG. 8C shows a top view of support element 800 integrally formed with a shim 470 as shown in FIG. 8A.

FIG. 8C is a top view of support element 800 shown in FIG. 8C.

Figure 9:
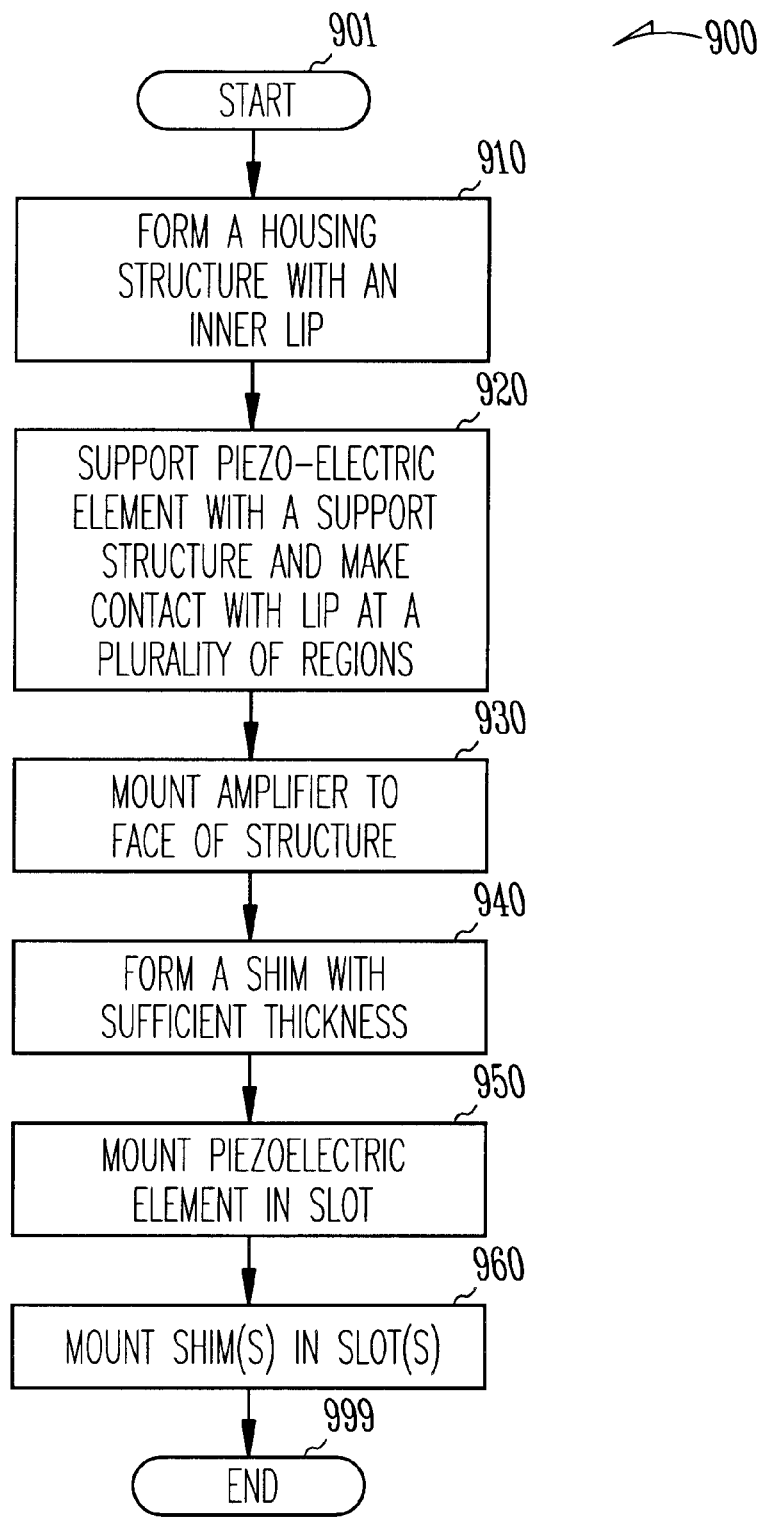
FIG. 9 shows a flowchart detailing a method 900 for fabricating a pressure-waveform sensor 100.

FIG. 9 is a flowchart detailing a method 900 for fabricating a pressure-waveform sensor (e.g., sensor 100). The method includes the steps of forming 910 a housing structure 110 with an inner lip 112, and supporting 920 a cantilevered piezoelectric element 170 with a support structure 400 such that contact is made with the inner lip 112 at a plurality of regions in order to level the piezoelectric element 170 relative to the inner lip 112. Some embodiments of method 900 further includes a step of mounting 930 an amplifier 190 to a face of the support structure 400.

Figure 10:
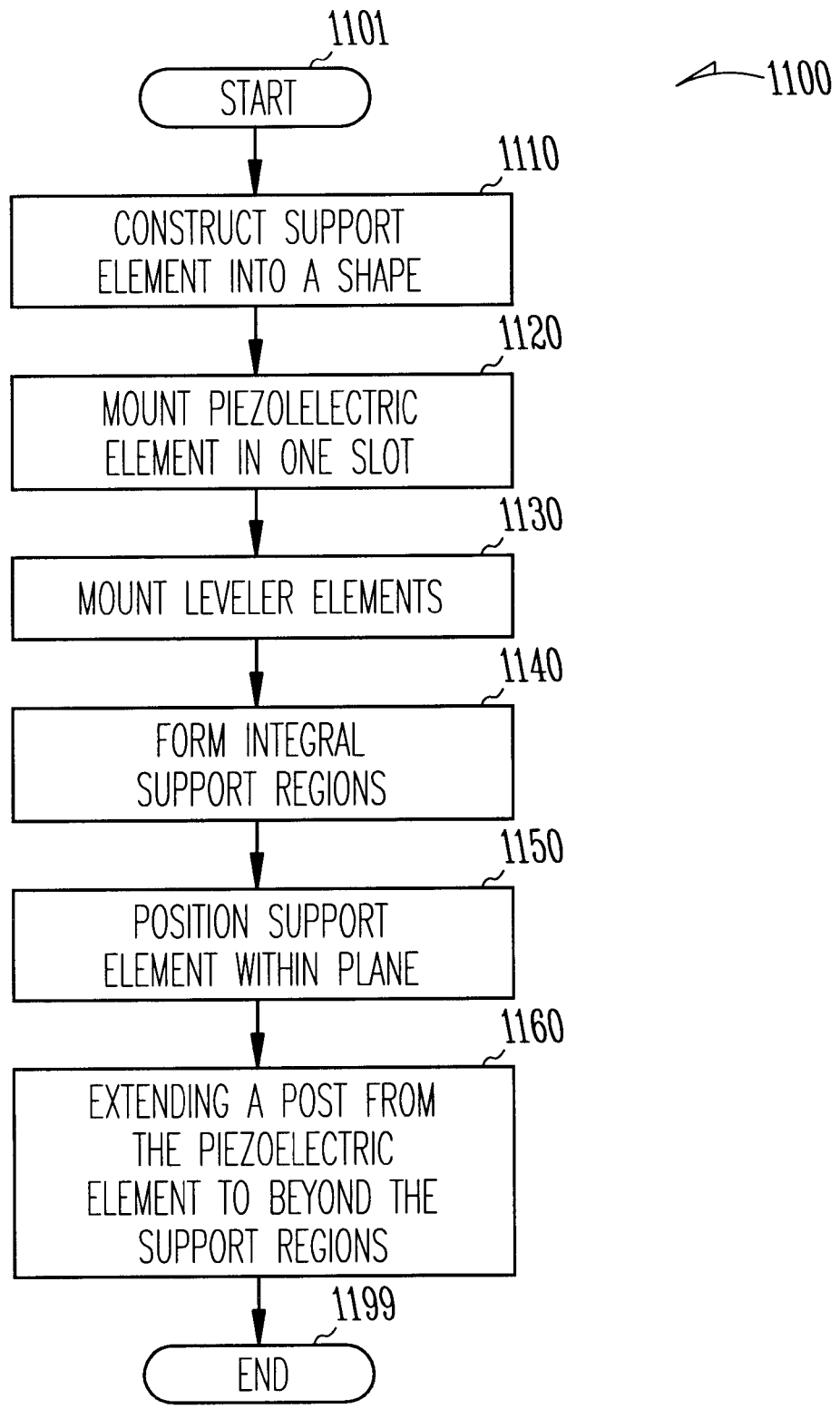
FIG. 10 shows a flowchart of a method 1100 for fabricating a pressure-waveform sensor leveler element 400 (alternatively 500, 600, 700, or 800).

FIG. 10 is a flowchart detailing a method 1100 for constructing a pressure-waveform sensor leveler support element (e.g., elements 400, 500, 600, 700, or 800). The method includes a step 1110 of constructing support element in a shape to provide support regions, a step 1120 of mounting a cantilevered piezoelectric element in a first one of the slots. In some such embodiments, the method further includes a step 1130 of mounting leveler elements in one or more slots to provide one or more support regions. In some embodiments, the method further includes a step 1140 of forming the support regions as integral to the support element.

In some embodiments, the method includes a step 1150 of positioning the support regions of the support element and the piezoelectric element to be coplanar; and In some embodiments the method includes a step 1160 of extending a post from the piezoelectric element to beyond the support regions to contact a diaphragm.

In some embodiments, sensor 100 further includes a configuration where support regions 421 of the support element 400 and piezoelectric element 170 are coplanar. In other embodiments, sensor 100 further includes post 172 secured to cantilevered piezoelectric element 170. In addition, post 172 extends below the plane of support regions 421.

Except for the leveling features of support elements (400, 500, 600, 700, and 800) and other features described herein, other aspects of various embodiments of sensor 100 are made according to the description and instructions in patent application Ser. No. 09/045,018 entitled "SENSOR AND METHOD FOR SENSING ARTERIAL PULSE PRESSURE" mentioned above.

Conclusion

Described above is a method and an apparatus for fabricating a pressure-waveform sensor with a support element 400.

One embodiment provides a pressure-waveform sensor 100 having a housing 110, a support element 400 (or, in other embodiments, support element 500, 600, 700 or 800) and a piezoelectric element 170 having a first end 168 secured between the support element 400 and the housing 110, and a second end 169 in a cantilevered orientation 171. The support element 400 and the piezoelectric element 170 together provide a plurality of support regions 421, 441 to level the piezoelectric element 170 and the support element 400 relative to the housing 110.

In one embodiment, one or more of the plurality of support regions 421 are formed with a shim 460 having a thickness equal to a thickness of the piezoelectric element 170. In some such embodiments, a diaphragm 120 is displacementally coupled to the second end 169 of the piezoelectric element 170.

In some embodiments of the pressure-waveform sensor 100, the support element 400 includes a ring 180 having two slots 420 and one slot 440 spaced apart on one face of the ring, and having the piezoelectric element 170 mounted to a first one of the slots 440. In one such embodiment, the ring 400 further includes one or more wire leveler elements 410 mounted in a second slot 420 and a third slot 420 of the three slots to provide two of the support regions. In one such embodiment, the support regions are 421 are formed using shims having a thickness equal to the piezoelectric element 170 and/or a sufficient thickness to level the piezoelectric element 170 relative to the housing 110.

In some embodiments of the pressure-waveform sensor 100, the support element 400 has a first face region 440 for attaching to the first end 168 of the piezoelectric element 170, and a second face region 470 elevated relative to the first face region 440 to provide one or more of the plurality of support regions 421. In one such embodiment, the support region or regions 421 of the second face region 470 are integral to the support element 400.

In some embodiments, the sensor 100 further includes a configuration where the support regions of the support element 400 and the piezoelectric element 170 are coplanar. In other embodiments, the sensor 100 further includes a post 172 secured to the cantilevered piezoelectric element 170. In addition, the post 172 extends below the plane of the support region 421.

In some embodiments, the sensor 100 further includes an amplifier 190 secured to a face of support element 400 opposite to the piezoelectric element 170.

Another aspect of the present invention provides a method 900 for fabricating a pressure-waveform sensor. The method includes the steps of forming 910 a housing structure 110 with an inner lip 112, and supporting 920 a cantilevered piezoelectric element 170 with a support element 400 such that contact is made with the inner lip 112 at a plurality of points in order to level the piezoelectric element 170 relative to the inner lip 112.

Some embodiments of method 900 further includes a step 930 of mounting an amplifier 190 to a face of the support structure 400. In other embodiments, the method further includes a step 940 of forming a shim having sufficient thickness to level the piezoelectric device relative to the housing structure 110.

Another aspect of the present invention provides a method 1100 for fabricating a pressure-waveform leveler support element 400 500 700 or 800. The method includes a step 1110 of constructing support element in a shape to provide support regions, a step 1120 of mounting a cantilevered piezoelectric element in a first one of the slots. In some such embodiments, the method further includes a step 1130 of mounting leveler elements in one or more slots to provide one or more support regions. In some embodiments, the method further includes a step 1140 of forming the support regions as integral to the support element.

In some embodiments, the method includes a step 1150 of positioning the support element and the piezoelectric element to be coplanar relative to the housing structure.

In some embodiments, the method includes a step 1150 of positioning the support regions of the support element and the piezoelectric element to be coplanar; and In some embodiments the method includes a step 1160 of extending a post from the piezoelectric element to beyond the support regions to contact a diaphragm.

In various embodiments, support element 400 is made of stainless steel, plastic or ceramic. Stainless steel is a conductor (and in some such embodiments, an insulating layer 179 is used (see FIG. 1), whereas plastic and ceramic are electrical insulators (and in those embodiments, layer 179 is not needed).

In one embodiment of support element 400, a slot 184 is machined into one face of ring 180, and slot 440 and two slots 420 (e.g., three identical slots spaced 120 degrees from one another) machined into the opposing face of ring 180. The three slots are filled with epoxy 179. Three identical smaller and shallower slots are then machined into the epoxy (in one embodiment, slot 184 is used to register, align, and center the smaller slots in the epoxy to the center of the slots 420 and 440). Element 170 is epoxied into slot 440, and spacers 410 are epoxied into the slots 420. If a defect is discovered in the epoxy of slot 440, then one of the slots 420 (which are identical to the desired slot 440) is instead used for holding cantilevered piezoelectric element 170, and the spacer 410 is epoxied to slot 440 (since defects that affect piezoelectric element 170 may not degrade the function of a spacer 410. In one embodiment, the assembled support element 400 is then inserted into housing 110, and then conductive epoxy is placed into slot 184 on top of a ground wire from amplifier 190, thus electrically grounding (connecting) support element 400 to housing 110 and to the ground wire from amplifier 190 (with no epoxy between piezoelectric element 170 and shelf 112, which are electrically coupled by contact).

It is to be understood that the above description is intended to be illustrative, and not restrictive. Although numerous characteristics and advantages of various embodiments of the present invention have been set forth in the foregoing description, together with details of the structure and function of various embodiments, many other embodiments and changes to details will be apparent to those of skill in the art upon reviewing the above description. The scope of the invention should, therefore, be determined with reference to the appended claims, along with the full scope of equivalents to which such claims are entitled.

What is claimed is:

1. A pressure-waveform sensor comprising:

a housing;

a support element; and a piezoelectric element having a first end secured between the support element and the housing, and a second end in a cantilevered orientation;

wherein the support element and the piezoelectric element together form a plurality of support regions to level the piezoelectric element relative to the housing.

2. The sensor according to claim 1, wherein one or more of the plurality of support regions are formed with one or more shims having a thickness sufficient to level the piezoelectric element relative to the housing.

3. The sensor according to claim 2, wherein each one of the one or more shims has a thickness equal to a thickness of the piezoelectric device.

4. The sensor according to claim 2, wherein each one of the one or more shims has a cylindrical shape.

5. The sensor according to claim 1, further comprising a diaphragm displacementally coupled to the second end of the piezoelectric element.

6. The sensor according to claim 1, wherein the support element comprises a ring, the ring including three slots spaced apart on one face of the ring, and having the piezoelectric element mounted to a first one of the slots.

7. The sensor according to claim 6, wherein the ring further comprises wire leveler elements mounted in a second and a third of the three slots to provide two of the support regions.

8. The sensor according to claim 5, wherein the ring further comprises wire leveler elements mounted in a second and a third of the three slots to provide two of the support regions.

9. The sensor according to claim 1, wherein the support element comprises a first face region for attaching to the first end of the piezoelectric element, a second face region elevated relative to the first face region to provide one or more of the plurality of support regions.

10. The sensor according to claim 9, wherein the support regions of the second face region are integral to the support element.

11. The sensor according to claim 1, wherein the support regions of the support element and the piezoelectric element are coplanar.

12. The sensor according to claim 1, further comprising a post secured to the cantilevered piezoelectric element; wherein the support regions of the support element and the piezoelectric element are coplanar and wherein the post extends below the plane of the support regions.

13. The sensor according to claim 1, further comprising an amplifier secured to a surface of the support element by epoxy.

14. The sensor according to claim 1, wherein the support element comprises a ring, the ring including a plurality of slots spaced apart on one face of the ring, and having the piezoelectric element mounted to a first one of the slots, and further including leveler elements mounted in a second and a third of the three slots to provide two of the support regions.

15. The sensor according to claim 1, wherein the support element comprises a ring, the ring including three slots spaced apart on one face of the ring, and having the piezoelectric element mounted to a first one of the slots.

16. An arterial-pulse sensor comprising:

a rigid housing having a diaphragm;

an electrical amplifier mounted within the housing;

a piezoelectric element mounted within the housing, mechanically coupled to the diaphragm, and electrically coupled to the amplifier; and support means for leveling the piezoelectric element within the housing.

17. The sensor according to claim 16, wherein the piezoelectric element is mechanically coupled to a vibrating portion of the diaphragm using a rigid connecting element.

18. The sensor according to claim 16, further comprising:

a support element, wherein the piezoelectric element has a first end secured between the support element and the housing, and wherein the support means for leveling functions to level both the support element and the piezoelectric element within the housing.

19. A pressure-waveform sensor comprising:

a housing;

a support element; and a piezoelectric element having a first end secured between the support element and the housing, and a second end in a cantilevered orientation, wherein the support element has a plurality of slots, and the piezoelectric element is secured in one of the slots, and a shim is secured in each one of one or more others of the slots to level the piezoelectric element relative to the housing.

20. The sensor according to claim 18, wherein each one of the one or more shims has a rectangular cross-section.

21. The sensor according to claim 18, wherein each one of the one or more shims has a cylindrical shape.

22. A pressure-waveform sensor comprising:

a housing;

a support element; and a piezoelectric element having a first end secured between the support element and the housing, and a second end in a cantilevered orientation, wherein the support element has one or more raised areas and a slot, and the piezoelectric element is secured in the slot to level the piezoelectric element relative to the housing.

* * * * *

UNITED STATES PATENT AND TRADEMARK OFFICE
CERTIFICATE OF CORRECTION

PATENT NO. : 6,331,161 B1                                         Page 1 of 1
DATED      : December 18, 2001
INVENTOR(S) : Charles F. Chesney, Michael Terry Riggs and Charles A. Lemaire It is certified that error appears in the above-identified patent and that said Letters Patent is hereby corrected as shown below:

Column 6,
Line 34, insert -- . -- after "thereof".

Column 10,
Line 53, insert -- 600 --, between "500" and "700".

Column 13,
Line 10, claim No. "18" and insert -- 19 --, thereof.
Line 12, claim No. "18" and insert -- 19 --, thereof.

Signed and Sealed this

Twentieth Day of August, 2002

Attest:

JAMES E. ROGAN
Attesting Officer                Director of the United States Patent and Trademark Office